United States Patent [19]

Akamatsu et al.

[11] Patent Number: 4,745,099

[45] Date of Patent: May 17, 1988

[54] PHARMACEUTICAL COMPOSITION FOR THE TREATMENT OF THE ANEMIA OF MALIGNANT TUMORS

[75] Inventors: Ken-ichi Akamatsu, Tokyo; Masayoshi Ono, Saitama, both of Japan

[73] Assignee: Chugai Seiyaku Kabushiki Kaisha, Tokyo, Japan

[21] Appl. No.: 825,223

[22] Filed: Feb. 3, 1986

[30] Foreign Application Priority Data

Feb. 6, 1985 [JP]  Japan ................... 60-21163

[51] Int. Cl.$^4$ ............................. A61K 37/10
[52] U.S. Cl. ....................... 514/8; 514/814
[58] Field of Search ................ 424/99; 514/8, 814

[56] References Cited

U.S. PATENT DOCUMENTS 4,254,895  3/1981  Fisher et al. ............... 424/1.1
4,303,680  12/1981  Takezawa et al. ........... 424/99

FOREIGN PATENT DOCUMENTS

148605A2  7/1985  European Pat. Off. .
2467214  5/1981  France ................... 424/99
2501692  9/1982  France ................... 424/99
2135676A  5/1984  United Kingdom .

OTHER PUBLICATIONS

Merck Index, 10th Edition, p. 533, No. 3632.

*Primary Examiner*—John Rollins
*Attorney, Agent, or Firm*—Morgan & Finnegan

[57] ABSTRACT

A pharmaceutical composition for the treatment of the anemia of malignant tumors comprising a therapeutically effective amount of human erythropoietin (EPO) in a parenterally acceptable vehicle is disclosed. Human EPO may be extracted from human urine or also be prepared by expressing in a host cell the gene coding for the amino acid sequence of human EPO.

1 Claim, 4 Drawing Sheets

PHARMACEUTICAL COMPOSITION FOR THE TREATMENT OF THE ANEMIA OF MALIGNANT TUMORS

The present invention relates to a pharmaceutical composition for the treatment of the anemia of malignant tumors that comprises a therapeutically effective amount of human erythropoietin (hereinafter referred to as "human EPO") in a parenterally acceptable vehicle.

The term "human EPO" as used hereinafter means a polypeptide having the amino acid sequence inherent in human beings, with or without sugar chains. Examples of the human EPO include one that is derived from human urine (hereinafter referred to as "human urinary EPO"), one obtained by expressing in a host cell the gene coding for the amino acid sequence of human EPO (this type of human EPO is hereinafter referred to as "human rEPO"), one obtained from a tissue culture of human kidney cancer cells, and one obtained by cultivating a hybridoma resulting from cell fusion of a human cell line having the ability to produce human EPO. The term "erythropoietin" (hereinafter referred to as "EPO") will mean a trace physiologically active substance that acts on erythroblastic stem cells present not only in humans but also in other animals so as to accelerate the differentiation of such stems cells into mature erythrocytic cells, and proliferation of the latter. While numerous studies on human urinary EPO have been reported, the pharmaceutical utility of human EPO still remains unknown in many respects.

High incidence of anemia as one of the complications in cancer-bearing patients has been known for many years (see, for example, Miller, A. et al.; J. Clin. Invest. 35, 1248 (1956)), and severe anemia associated with malignancy is of particular clinical concern in the treatment of the disease. Many hypotheses have been proposed for explaining the mechanism behind the development of anemia, and they include the blockade of iron in the reticuloendothelial system due to abnormal iron metabolism, impaired iron release, spleen involvement, impaired EPO production, hemolysis, and disorders in hemopoietic stem cells. In the case of the anemia of malignant tumors, possible causes include hemorrhage resulting from abnormal tumor growth, the blockade of reticuloendothelial iron release, infiltration of bone marrow with tumor cells, hemolysis due to impaired microvessels and autoimmune diseases, bone marrow suppression resulting from treatment with anti-tumor agents or radiotherapy, as well as chronic inflammation. The plasma EPO levels in cancer-bearing patients have been reported to be equal to or lower than normal levels (see, for example, Zucker, S. et al., J. Clin. Invest., 53, 1132 (1974); Douglas, S. W. et al., Blood, 45, 55 (1975); Firat, D. et al., Cancer Res., 31, 1355 (1971); Ward, H. P. et al., J. Clin. Invest., 50, 332 (1971); and Degowin, R. L. et al., J. Lab. Clin. Med., 94, 303 (1979)). However, in the absence of any corelation between the decrease in the plasma EPO levels and the degree of anemia in malignancy and in view of the fact that most cancer-bearing patients suffer from dysfunction of bone marrow, some researchers propose that the principal cause of the anemia of malignancy is not impaired erythropoietin production but more probably is impaired erythropoietic ability in the bone marrow due to hyporesponsiveness to EPO. Therefore, in view of the proposed mechanism for the development of anemia in malignancy, it has been very doubtful that administration of human EPO to patients with the anemia of malignancy is effective for the purpose of treating the disease. As already mentioned, numerous papers exist that report the various functions of human urinary EPO but nobody has demonstrated by in vivo experimentation with humans or animals that human urinary EPO and other types of human EPO are effective as therapeutic agents for the treatment of anemia in malignancy.

The present inventors prepared a highly pure form of human urinary EPO and they also obtained human rEPO by expressing in a host cell the gene coding for the amino acid sequence of human EPO. Using these two types of human EPO, the inventors studied their therapeutic effects for anemia in cancer-bearing animals. To their great surprise, these types of human EPO turned very effective against the anemia, and therefore, the inventors concluded that they are useful as therapeutic agents for the treatment of anemia in malignancy. The present invention has been accomplished on the basis of this finding.

The principal object, therefore, of the present invention is to provide a novel pharmaceutical composition for the treatment of anemia in malignancy that comprises a therapeutically effective amount of human EPO in a parenterally acceptable vehicle.

Figure 1:
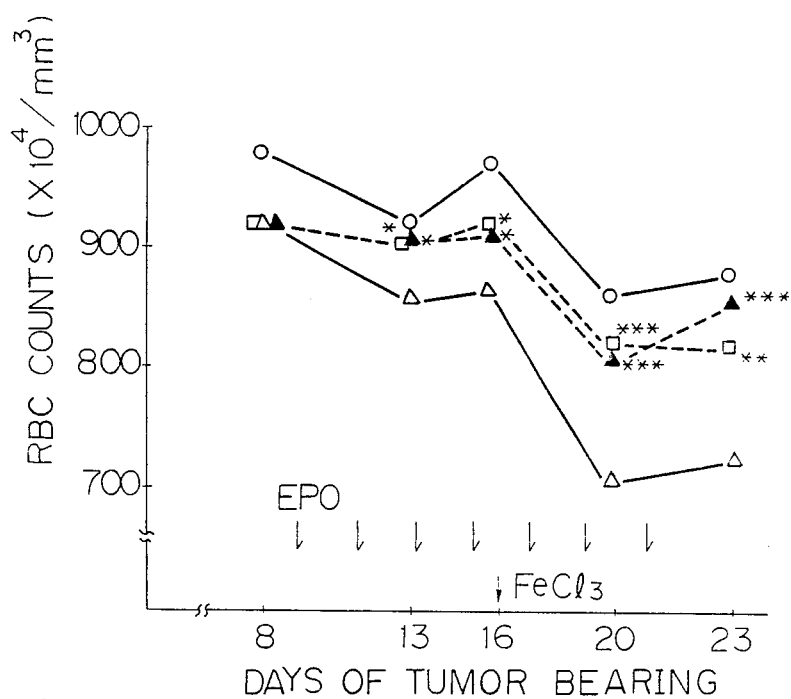
FIG. 1 shows the effect of human EPO administration on the peripheral erythrocyte counts (RBC) in mice bearing Lewis lung carcinoma.

In FIGS. 1 to 4, o-o refers to the group of noncancer bearing mice, ▲-▲ the group of cancer-bearing mice to which only the solvent was administered, the group of cancer-bearing mice to which human urinary EPO was administered, and □-□ the group of cancer-bearing mice to which CHO cell derived human rEPO was administered. The asterisks in each figure represent levels of significance in differences from the cancer-bearing mouse group to which only the solvent was administered: $*P<0.05$, $P<0.01$, and $*P<0.001$.

The types of human EPO that are incorporated in the composition of the present invention as the active ingredient may be prepared by a variety of means. For example, human urinary EPO may be extracted from normal human urine or the urine of plasma (including serum) of patients with hypoplastic anemia (T. Miyake et al., J. B. C., 252, 5558 (1977); and J. P. Lewin et al., J. Lab. Clin. Med., 66, 987 (1965)). Human rEPO may be prepared by genetic engineering procedures comprising obtaining a messenger RNA (mRNA) corresponding to the amino acid sequence of human EPO, preparing a recombinant DNA using the mRNA, and expressing the DNA gene in a suitable host cell such as a bacterium (e.g. E. coli), a yeast, or a plant or animal cell line (see, for example, Sylvia, L. H., Proc. Natl. Acad. Sci., USA, 81, 2708 (1984)). While various animal cell lines are available as host cells, cultured cell lines derived from humans or mammalian animals are preferred and they include COS cells, Chinese hamster ovary (CHO) cells, and mouse C-127 cells. Human EPO may also be prepared from, for example, tissue cultures of human kidney cancer cells (Unexamined Published Japanese Patent Application No. 55790/1979), from human lymphoblastic cells having the human EPO producing ability (Unexamined Published Japanese Patent Application No. 40411/1982), and from a culture of the hybridoma obtained by cell fusion of a human cell line. Any of the types of human EPO that are prepared by these methods are useful in the present invention so long as they enable the proliferation of mature red blood cells having sufficient oxygen transport to be useful in the treatment of anemia in malignancey.

The human EPO present in the urine or the supernatant of culture obtained by the aforementioned methods may be further concentrated and purified by routine isolation and purification procedures such as, for example, precipitation with an organic solvent (e.g. benzoic acid, ethanol, acetone or tannic acid), salting out with ammonium sulfate, etc., dialysis by, for example, vacuum concentration, chromatographic techniques (e.g. gel permeation chromatography, ion-exchange chromatography and affinity chromatography), and electrophoretic techniques (e.g. isoelectric electrophoresis and gel electrophoresis). These isolation and purification procedures may be employed either independently or in combination.

The human EPO thus prepared may be stored either frozen or in a dehydrated state attained by freeze-drying, vacuum drying or other suitable methods. Alternatively, an aqueous solution containing the human EPO may be mixed with a water-soluble salt or a hydrophilic organic solvent to precipitate the active ingredient, which then is dehydrated for storage purposes. If desired, the human EPO may be dissolved in a suitable buffer solution and aseptically filtered such as through a Millipore filter to prepare an injection.

The pharmaceutical composition of the present invention for the treatment of anemia in malignancy may be mixed with conventional anemia treating agents such as chalybeates, vitamin $B_{12}$ and androgens, either in a dosage form or just before use. Illustrative chalybeates include dried ferrous sulfate, iron fumarate, iron dextran, iron gluconate, iron glucuronate and iron orotate.

The dosage and frequency of administration of the human EPO incorporated in the therapeutic composition of the present invention may be determined depending upon the condition of the patient under therapeutic regimen. In ordinary cases, a preparation containing 0.1–500 μg, preferably 5–100 μg, of human EPO may be administered to an adult in 1–7 doses for one week, assuming a human erythropoietin activity of $9 \times 10^4$ units per mg.

The pharmaceutical composition of the present invention for the treatment of anemia in malignancy may contain a stabilizer selected from among polyethylene glycol, proteins, sugars, amino acids, inorganic salts, organic salts and sulfur-containing reducing agents. These stabilizers may be employed either individually or in combination. They are preferably incorporated in the composition of the present invention in an amount ranging from 0.11 to 10,000 parts by weight per part by weight of human EPO. If two or more stabilizers are used, it suffices that the total of their amounts is within the range specified above. These stabilizers are used in the form of an aqueous solution containing a corresponding amount of a specific stabilizer to provide the appropriate concentration and pH. This aqueous solution is adjusted to have an osmotic pressure ratio of 0.1–3.0, preferably 0.8–1.2. The pH of the aqueous solution is adjusted to a value between 5.0 and 9.0, preferably between 6 and 8.

The composition of the present invention may be prepared in a dosage form in the presence of an adsorption preventing agent.

REFERENCE EXAMPLE 1: PREPARATION OF HUMAN URINARY EPO

Step (1): Partial purification from human urine

Urine from patients with hypoplastic anemia was subjected to the procedures of T. Miyake et al. (J. B. C., 52, 5558 (1977)); viz., (1) deionization on a Sephadex G50 column, (2) adsorption on DEAE-cellulose in a batch system, (3) precipitation with ethanol, and (4) chromatography on a DEAE-agarose column. By these procedures, a partially purified form of human urinary EPO was obtained.

Step (2): Reverse phase chromatography

The partially purified human urinary EPO was dissolved in a 0.1% trifluoroacetic acid (Aldrich Chemical Co., Inc.) solution containing 24% propanol (Wako Pure Chemical Industries, Ltd.) and the solution was subjected to purification by HPLC with Hitachi Model 638-50. Absorption in the ultraviolet range at 280 nm and 220 nm was used as an indicator.

The so prepared sample was loaded onto a YMC-C8 column (6 mm × 30 cm, product of Yamamura Chemical Co., Ltd.) equilibrated with a 0.1% trifluoroacetic acid solution containing 24% n-propanol, and the column was eluted with the same equilibrating solution. After the unadsorbed fractions were eluted, the concentration of n-propanol was increased to 26% for eluting the active fractions. The fractions containing the EPO activity were collected and concentrated to a volume of 0.1–0.2 ml by ultrafiltration using Centricon-100 (trade name of Amicon).

Step (3): High-Performance molecular sieve chromatography

The concentrated sample was loaded onto a TSK-G300 SW column (7.8 mm × 60 cm, product of Toyo Soda Manufacturing Co., Ltd.) equilibrated with a 0.1% TFA solution containing 26% n-propanol, and the column was eluted with the same equilibrating solution. Peaks having the EPO activity were obtained at positions corresponding to molecular weights of 25,000–30,000. These active fractions were collected and freeze-dried. The fractions had a specific activity of about $9 \times 10^4$ units/mg.

The specific activities of the samples prepared in the respective steps (1) to (3) are listed in Table I.

TABLE I

| Step | Specific activity (U/mg) |
| --- | --- |
| (1) partial purification | 600 |
| (2) reverse phase chromatography | 10,000 |
| (3) high-performance molecular sieve chromatography | 90,000 |

Assay method: In accordance with the method of N. N. Iscove et al., J. Cell. Physiol., 83, 309 (1974).

REFERENCE EXAMPLE 2: PREPARATION OF HUMAN rEPO DERIVED FROM CHO CELLS

A plasmid incorporatinig the gene coding for the amino acid sequence of human EPO was expressed in Chinese hamster ovary cells (CHO cells) to produce human rEPO. The procedures employed are specifically described in Japanese Patent Application No. 281862/1984 (filed Dec. 27, 1984), entitled "Vector harboring accessory DNA for the transformation of eucaryotic cells". A summary of the procedures is given below.

The DNA from a lambda HEPOFL 13 clone incorporating the gene coding for the amino acid sequence of human EPO derived from fetal human liver cells was digested with EcoRI, and the recovered small EcoRI fragment harboring the gene coding for the amino acid sequence of human EPO was inserted into the EcoRI site of plasmid RKI-4. The plasmid then was incorporated into DHFR-deficient CHO cells so as to transform them. The transformed CHO cells were cultured in an alpha-medium deficient of nucleic acids. Cells harboring at least one DHFR gene were selected and employed in the production of human rEPO, with the concentration of methotrexate in the medium being increased incrementally. The human rEPO in the supernatant of the finally obtained culture had an activity of 20 units/ml.

The CHO cells were cultivated in a serum-free liquid culture medium for 3 days and pure human rEPO was isolated by the procedures employed in the preparation of pure human urinary EPO. The so obtained human rEPO was found to have an activity of 6,600 units/ml as measured by the method of Krystal et al. (J. Lab. Clin. Med., 97, 144 (1981)). SDS-polyacrylamide gel electrophoresis showed that this human rEPO was comprised of a single protein band. The human rEPO was mixed with 0.1% BSA and dialyzed against physiological saline to prepare samples for use in subsequent experiments.

Experiments: Therapeutic effects of human EPO for the treatment of anemia in malignancy 1. Preparation of cancer-bearing mice Small square pieces (1-2 mm on one side) of the mouse tumor cell lines listed below were transplanted under the skin of the flanks of 6-week old male mice. At 12-16 days of transplantation, blood was partially withdrawn from dorsal metalarsal veins for determining erythrocyte counts (RBC), hemoglobin content (HGB) and leukocyte counts (WBC) with a Coulter counter (Toa Medical Electronics Co., Ltd.). The results are summarized in Table II.

| Tumor cell lines | Mice |
|---|---|
| Ca 755 (mammary adenocarcinoma) | C57BL/6N (available from Japan Charles River Co., Ltd.) |
| Lewis lung carcinoma (lung cancer) | C57BL/6N (available from Japan Charles River Co., Ltd.) |
| C3MC 2 (fibrosarcoma) | C3H/HeN (available from Japan Charles River Co., Ltd.) |

TABLE II

| Transplanted cell line | RBC ($\times 10^4$/mm$^3$) | (T/C %) | HGB (g/dl) | (T/C %) | WBC ($\times 10^4$/mm$^3$) | (T/C %) |
|---|---|---|---|---|---|---|
| Non-cancer bearing (control) | 929 | | 18.4 | | 153 | |
| Ca 755 | 521 | (56) | 12.2 | (66) | 59 | (39) |
| Lewis lung carcinoma | 803** | (86) | 17.5 | (95) | 172* | (112) |
| Non-cancer bearing (control) | 873 | | 18.6 | | 81 | |
| C3MC2 | 748* | (86) | 14.6** | (78) | 161* | (199) |

*P < 0.05
**P < 0.01

As Table II shows, all of the cancer-bearing mice were in the anemic state.

2. Therapeutic effects of human EPO for the treatment of anemia a. Lewis lung carcinoma transplanted mouse model Lewis lung carcinoma was transplanted in 6-week old male BDF1 mice (available from Japan Charles River Co., Ltd.) as in 1. At 8 days of transplantation, the tumor-bearing mice in which successful grafting was confirmed were divided into three groups each consisting of seven animals bearing the same size of tumor. At 9 days of transplantation, the three groups of mice were injected subcutaneously with human urinary EPO (10 units/mouse/day), CHO cell derived human rEPO (10 unites/mouse/day) and a solvent (0.5 ml/mouse/day of a dialyzate of RPMI 1640 medium containing 0.1% BSA solution) and seven injections were performed with a one-day interval given between injections.

At 16 days of transplantation, iron chloride (1 mg/mouse as Fe) was administered intraperitoneally to the groups of cancer-bearing mice for the purpose of iron supply. The control group consisted of seven non-cancer bearing BDF1 mice.

Figure 2:
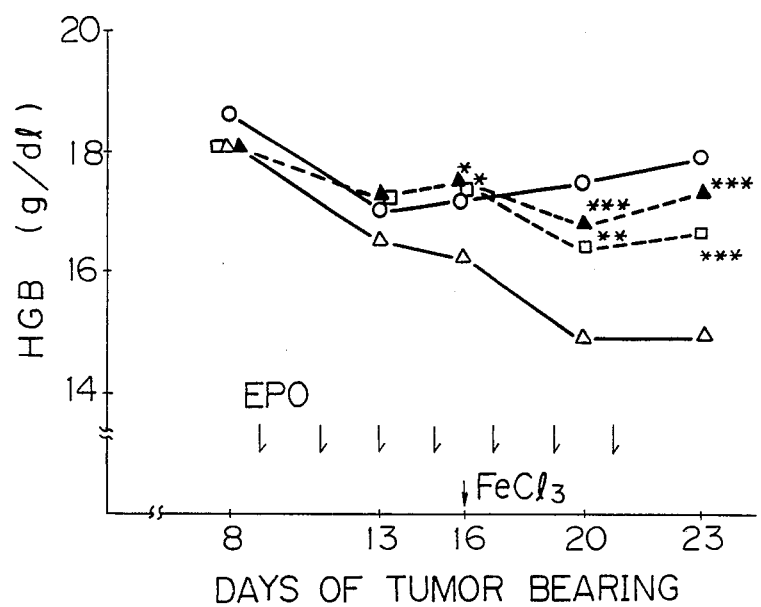
FIG. 2 shows the effect of human EPO administration on the peripheral hemoglobin content (HGB) in mice bearing Lewis lung carcinoma.

The profiles of erythrocyte counts (RBC) and hemoglobin (HGB) as a function of days after tumor transplantation are shown in FIGS. 1 and 2, respectively.

b. C3MC2 fibrosarcoma transplanted mouse model

C3MC2 fibrosarcoma was transplanted in 6-week old male C3H/HeN mice (available from Japan Charles River Co., Ltd.) as in 1. At 28 days of transplantation, the tumorbearing mice in which successful grafting was confirmed were divided into three groups each consisting of seven animals bearing the same size of tumor. At 29 days of transplantation, the three groups of mice were injected subcutaneously with human urinary EPO (10 units/mouse/day), CHO cell derived human rEPO (10 units/mouse/day) and a solvent (0.5 ml/mouse/day of a dialyzate of RPMI 1640 medium containing 0.1% BSA solution) and seven injections were performed with a one-day-interval given between injections. At 36 days of transplantation, ferric chloride (1 mg/mouse as Fe) was administered intraperitoneally to the groups of cancer-bearing mice for the purpose of iron supply. The control group consisted of seven non-cancer bearing C3H/HeN mice.

Figure 3:
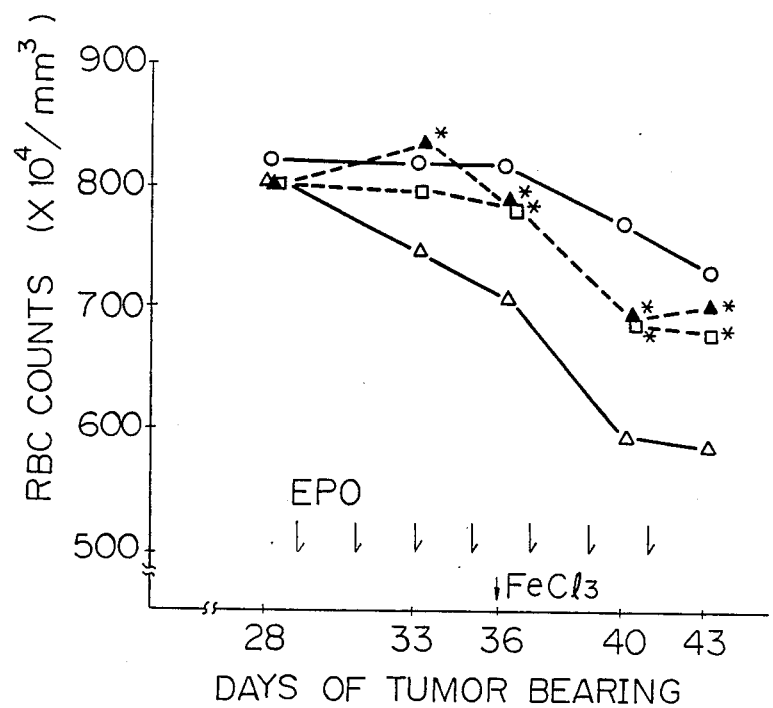
FIG. 3 shows the effect of human EPO administration on the peripheral erythrocyte counts (RBC) in C3MC2-bearing mice.
Figure 4:
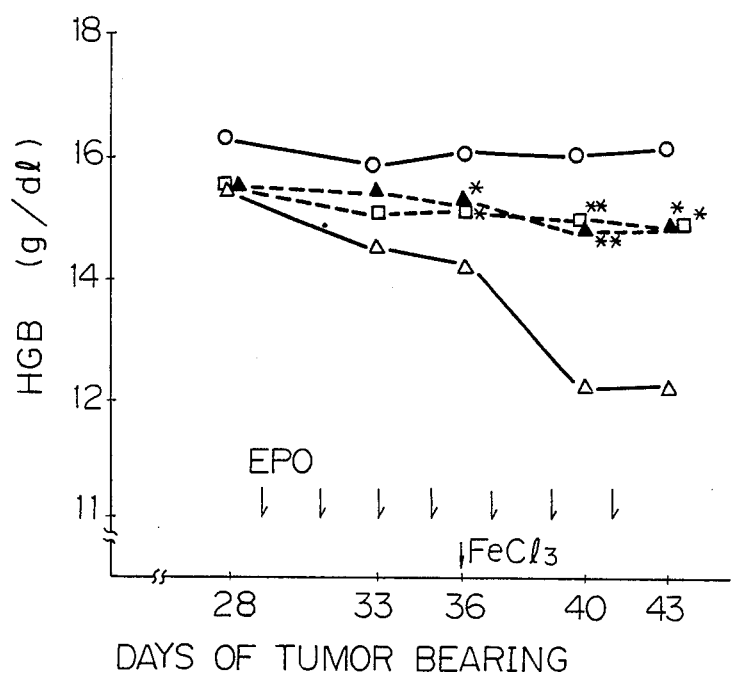
FIG. 4 shows the effect of human EPO administration on the peripheral hemoglobin content (HGB) in C3MC2-bearing mice.

The profiles of erythrocyte counts (RBC) and hemoglobin (HGB) as a function of days after tumor transplantation are shown in FIGS. 3 and 4, respectively.

As FIGS. 1 to 4 show, the degree of anemia in the group of mice to which only the solvent was administered increased with the lapse of time after tumor transplantation, but significant alleviation of anemia was observed in the groups of cancer-bearing mice to which human EPO was administered. The two types of human EPO had no toxicity under the experimental conditions used.

The following examples are provided for the purpose of further illustrating the present invention but are by no means taken as limiting.

EXAMPLE 1

A solution was aseptically prepared from the formulation indicated below.

| Ingredients | Amount (parts by weight) |
| --- | --- |
| CHO cell derived human rEPO | 1 |
| Human serum albumin | 100 |
| Distilled water for injection to make | 100,000 |

The solution was distributed among vials and freeze-dried, followed by the sealing of the vials.

EXAMPLE 2

Freeze-dried preparations were made as in Example 1 except that the human serum albumin was replaced by 100 parts by weight of dextran 40.

EXAMPLE 3

An aqueous solution containing mannitol (5 g), human urinary EPO (1 mg), human serum albumin (100 mg), sodium acetyltryptophan (2.154 mg) and sodium caprylate (1.33 mg) in 100 ml was prepared aseptically. Small portions (1 ml) of the solution were put into vials and freeze-dried, followed by the sealing of the vials.

EXAMPLE 4

An aqueous solution containing human urinary EPO (1 mg), polyethylene glycol 4000 (500 mg), ethylene oxidepropylene oxide copolymer (30 mg) and sodium chloride (800 mg) in 100 ml of a 0.05 M phosphate buffer solution (pH 7.0) was prepared aseptically. Small portions (1 ml) of the solution were put into ampules, which then were sealed by fusion.

EXAMPLE 5

An aqueous solution containing CHO cell derived human rEPO (0.5 mg), glycine (1 g) and sorbitol (1 g) in 50 ml of a 0.05 M phosphate buffer solution (pH 7.0) was prepared aseptically. Small portions (0.5 ml) of the solution were put into vials and freeze-dried, followed by the sealing of the vials. A 0.1% aqueous solution of methyl cellulose was also prepared aseptically and 1-ml portions of the solution were put into ampules for making solubilizing media.

EXAMPLE 6

An aqueous solution containing human urinary EPO (1 mg), human serum albumin (50 mg) and mannitol (500 mg) in 100 ml was prepared aseptically. Small portions (1 ml) of the solution were put into vials and freeze-dried, followed by the sealing of the vials. An aqueous solution containing ferric gluconate (3 g) and NaCl (2.7 g) in 300 ml was also prepared aseptically, and 3-ml portions of this solution were put into ampules which then were sealed by fusion. The content of one vial was transferred into one ampule and a complete solution was obtained by thorough mixing. The solution was injected intravenously over time (2-3 minutes).

What is claimed is:

1. A method for treating the anemia of malignant tumors in a patient who is suffering from anemia of malignant tumors which comprises administering to said patient a therapeutically effective amount of human erythropoietin for treating anemia of malignant tumors in a pharmaceutically acceptable carrier.

* * * * *

UNITED STATES PATENT AND TRADEMARK OFFICE
CERTIFICATE OF CORRECTION

PATENT NO.   :   4,745,099
DATED        :   May 17, 1988
INVENTOR(S)  :   Ken-ichi Akamatsu and Masayoshi Ono It is certified that error appears in the above-identified patent and that said Letters Patent is hereby corrected as shown below:

Column 2, line 40, the figure symbol "▲-▲" should appear as -- Δ-Δ --. Column 2, line 41, the blank space preceding "the group" should contain the figure symbol -- ▲-▲ --.

Signed and Sealed this

Ninth Day of April, 1991

Attest:

HARRY F. MANBECK, JR.

Attesting Officer

Commissioner of Patents and Trademarks